United States Patent [19]

Bichon

[11] Patent Number: 4,506,672
[45] Date of Patent: Mar. 26, 1985

[54] SHEATHED SURGICAL SUTURE FILAMENT AND METHOD FOR ITS PREPARATION

[75] Inventor: Daniel Bichon, Gaillard, France

[73] Assignee: Assut S.A., Carouge-GE, Switzerland

[21] Appl. No.: 279,972

[22] PCT Filed: Nov. 21, 1980

[86] PCT No.: PCT/EP80/00145
§ 371 Date: Jun. 30, 1981
§ 102(e) Date: Jun. 30, 1981

[87] PCT Pub. No.: WO81/01368
PCT Pub. Date: May 28, 1981

[30] Foreign Application Priority Data

Nov. 23, 1979 [CH] Switzerland .................. 10449/79

[51] Int. Cl.³ ............................................. A61L 17/00
[52] U.S. Cl. ........................... 128/335.5; 128/DIG. 8
[58] Field of Search ..................... 128/335.5, DIG. 8; 3/1; 424/19; 428/375, 378; 427/2

[56] References Cited

U.S. PATENT DOCUMENTS

| 3,166,073 | 1/1965 | Kronenthal | 128/335.5 |
| 3,512,183 | 5/1970 | Sharp et al. | 3/1 |
| 3,896,814 | 7/1975 | Vivien et al. | 128/335.5 |
| 3,987,797 | 10/1976 | Stephenson | 128/335.5 |

Primary Examiner—Ben R. Padgett
Assistant Examiner—T. J. Wallen
Attorney, Agent, or Firm—Finnegan, Henderson, Farabow, Garrett, & Dunner

[57] ABSTRACT

Catgut suturing filament protected by a flexible polymer sheath that is slowly hydrolytically degradable and impervious to body fluid degratative enzymes. The sheath is prepared by coating the catgut filament with an isocyanate capped polyhydroxylated polyester followed by curing.

10 Claims, 2 Drawing Figures

SHEATHED SURGICAL SUTURE FILAMENT AND METHOD FOR ITS PREPARATION

FIELD OF THE INVENTION

The present invention concerns a collagen or catgut suture filament coated with a protective flexible sheath made of an adherent polymeric resin that can be degraded hydrolytically but is enzymatically stable. It also concerns a method for its preparation.

BACK-GROUND OF THE ART

It is well known that ordinary catgut is currently losing attention as a surgical suture filament because of its biodegradation properties which are not favorable. Indeed, it has been shown that, when catgut is in contact with the living tissues surrounding a wound which has been stitched, it degrades enzymatically and loses its mechanical properties quite rapidly. This drawback can be somewhat lessened by subjecting the collagen of the catgut to tanning with chromium salts, however, such procedure has disadvantages since chromium compounds are toxic. Further, catgut sutures, chromated or not, induce unwanted tissue reactions, especially for the first days, such reactions being much less significant with more modern suture materials.

Thus, there is now a tendency to more and more replace the catgut sutures by synthetic filaments or braids made of polyesters the degradation of which has a profile different from that of catgut since it is not enzyme catalyzed. In short, when such polyesters (polyoxyacetyl esters such as polyglycolic or polylactic esters) are used as suture material, they will retain their tensile properties longer than catgut (even chromium treated) although the overall resorption time is about the same. Details on these questions will be found in the following references: Encyclopedia of Polymer Science & Technology, Vol 1 (Supplement), p. 587–596. P. Y. Wang et al: Structural Requirements for the Degradation of Condensation Polymer in Vivo, Polymer Science & Technology, Plenum Press (1973). K. Sugimachi et al: Evaluation of Absorbable Suture Materials in Biliary Tract Surgery, CA 89, 30728y. E. L. Howes: Strength Studies of Polyglycolic Acid versus Catgut Sutures of the Same Size, CA 79. 57648c. A. B. Kovacs et al: Comparative Study of Tissue Reactions to Various Suture Materials (Catgut, Silk and Polyesters), CA 72, 11183z.

OBJECTS OF THE INVENTION

However, suture filaments made of synthetic polymers are presently much more expensive than catgut made of ruminant guts and it is highly desirable that catgut be revived by simple, effective and cheap means. Such means are an object of the present invention which provides a catgut suture filament coated with an adherent protective sheath made of a resin that is hydrolytically degradable but which is thick enough to shield the collagen catgut core from the action of enzymes for a period sufficient for the sutured wound to heal before the suture filament loses much of its intrinsic mechanical properties. In practice, the sheath can have a thickness of from a few tenths of a micron to several hundredths of microns, however, this thickness can be adapted at will depending on the needs. When a sore is stitched with such a sheathed suture filament, the sleeve degrades very slowly such that the wire retains its mechanical properties for a time sufficient for the wound to heal; then, when the sheath has finally been hydrolyzed, the catgut core is attacked by the body enzymes and is resorbed very quickly.

Another object of the present invention is to provide a suture filament with a homogeneous and soft surface which is substantially free from pinholes, such pinholes being possible sites for the body fluids enzymes to penetrate the sheath and degrade the filament.

Another object of the invention is to provide a sheathed catgut filament with controlable sheath resistance to hydrolysis, such control being possible by properly selecting the polymer resin of such sheath and the coating conditions.

Another object of the invention is to provide a suture filament with excellent surface properties such as "slickness" and "knot-pull" properties as well as resistance to "knot slippage" when moistened by body fluids.

Still another object of the invention is to provide suture filaments with sheaths that will slowly degrade during a first period of time sufficient for the wound to heal, the mechanical properties of the filament staying substantially constant for such period, and that will then be rapidly resorbed by the organism during a second period after which the suture remnants are naturally eliminated.

Another object of the invention is also to provide methods for manufacturing the above mentioned sheathed filaments.

Other objects will become apparent from the following detailed description of the invention.

DETAILED DESCRIPTION OF THE INVENTION

Figure 1:
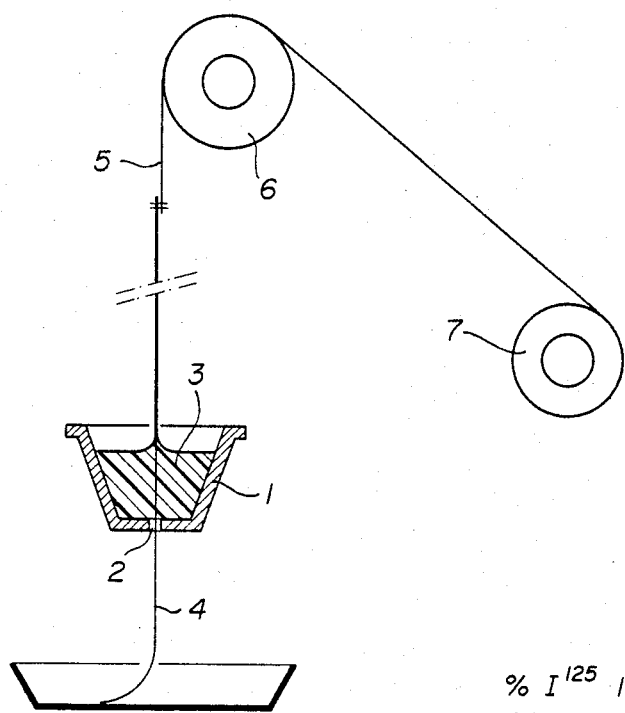

As a resin suitable for the sheath of the present suture filament, various polymers can be considered, the requirements being that they form thin flexible layers substantially resistant to enzyme degradation and only slowly hydrolyzed by the body tissues. As such, for instance, polyesters, preferentially reinforced by urethane and urea links, can be used. The base polyesters can have a general structure similar to that used for known synthetic sutures (polyhydroxyacids-esters) or be made from the polycondensation of selected diol-compounds with selected diacid-compounds. Among the diacids, oxalic acid, malonic acid, succinic acid, glutaric acid, adipic acid, pimelic acid, perfluoroadipic acid, 2,2-oxidiacetic acid, 2-oxoglutaric acid, D-tartaric acid and the like are convenient. Among the diols, the followings can be recited: aliphatic glycols of from 4 to 12 carbon atoms such as 1,4-butane-diol, 1,6-hexanediol and polyalkylene glycols (e.g. polyethylene glycols and polypropylene glycols) having 2 to 15 polyalkylene glycol units. It is important to note that the properties of the sheath are dependent on the proper selection of the diacid and the diol and also on some degree of cross-linking which can be introduced, if desired, as described hereinafter. In other words, the polymer can be made more or less flexible, more or less resilient, more or less smooth and more or less resistant to hydrolysis depending on the diacid selected, on the length of the alkylene or polyoxyalkylene segments and, of course, on the polymerization stoichiometry (molecular weight of the polyester diol resulting from the polycondensation). As an example of the above described possible variations, it can be mentioned that, when using a given diol, a sheath made from a polyester-polyurethane-polyurea resin containing oxalic acid is less resistant to hydrolysis than the corresponding resin containing, instead, 2,2-oxydiacetic acid, the latter being itself less resistant than the corresponding polymer based on glutaric acid.

Using a proper molecular range for the base polyester is also an important factor in the present invention. Being considered that the polycondensation can be schematized as follows:

$$HO\!-\!(\!-R\!-\!O\!-\!CO\!-\!R'\!-\!COO\!-\!)_{\overline{n}}ROH \quad (I),$$ it results that the base polyester diol molecular weight ($MW_{OH}$) will depend on the ratio $n/n+1$ and the nature of R (the alkylene or polyoxyalkylene segment of the diol) and of R' (the linking segment of the diacid). Thus, for instance, using 0.373 mole of 2,2-oxydiacetic acid and 0.391 mole of diethyleneglycol gives, after calculation from the above formula $n/n+1=373/391$, $n=20$ from which the molecular weight $MW_{OH}$ of formula I ($R=R'=-(CH_2)_2-O-(CH_2)_2-$; $MW_R=MW_{R'}=80$) is found to be 5074. In general, number average molecular weights determinations by analysis are in rather near agreement with the above predicted values.

In the practice of the present invention, high molecular weights (i.e. n being in the range of 15 or more) are not advantageous unless some degree of cross-linking is present. Such cross-linking can be introduced by using, in admixture with the diol, a proportions of a polyol, e.g. a triol, a tetrol or compounds containing more than three hydroxygroups; examples of such compounds are glycerol, trimethylol propane or hydrogenated sugars such as hexoses or pentoses, e.g. sorbitol. Indeed, in the absence of cross-links, polyesterglycols with molecular weights in the higher range (above 15 or more) will provide sheaths with somewhat too much elasticity; in other words, they will elongate too much under use stress relative to the catgut collagen core which effect is sometimes inconvenient. This can be remedied by either keeping n relatively low, e.g. between 2 and 10, preferably, or, when using polyesters glycol with n above 10 or more, adding from about 0.5 to 10% of the above triols or polyols. Naturally, in the practice of the present invention, mixtures of two or several diacids and/or diols can be used for preparing the base polyester glycol.

In the above polyester glycol condensation reaction scheme, it has been indicated that the condensation can be effected by heat in the presence of a catalyst ($AlCl_3$). It should be well understood that the conditions for effecting the polycondensation and obtaining the required polyester glycols are not novel per se and that classical polyester manufacturing conditions can be widely used such as a range of usual catalysts (or no catalyst, if suitable) and a range of usual polyesterification temperature and reaction times known to ordinary chemists.

The polyesters glycols used in the present invention can also be characterized by the OH number ($No_{OH}$) which amounts to the number of mg of potassium hydroxide corresponding to the quantity of —OH groups in one gram of the polymer. Thus, this value can be obtained from the inverse of the molecular weight $MW_{OH}$ times twice the molecular weight of KOH times one thousand. This value of $No_{OH}$ can also be obtained by analysis from a method in Anal. Chem. 35 (4), 571 (1963) which consists in weighing exactly an aliquot of the polyester-diol (m gram), blocking the OH groups by a known excess of phenylisocyanate, destroying the excess isocyanate with a known quantity of dibutylamine and back-titrating the excess dibutylamine with a $HClO_4$ solution. The analysis is carried out together with a control blank containing no polyester-diol; thus if x defines the amount of m mole of $HClO_4$ less used in the blank than in the sample (i.e. $x=x_s-x_b$ ml if $HClO_4$ is normal and the sample has consumed $x_s$ ml and the blank has consumed $x_b$ ml of such $HClO_4$ solution), then $No_{OH}=56.1x/m$ ($MW_{KOH}=56.1$). Thus, the above described measurement of the OH number if a convenient way to measure the molecular weight of the polyester diol for correlating with the molecular weight value derived from the relative proportions of the glycol and the diacid used in the polycondensation. The relationship is evidently $$MW_{OH} = \frac{56.1 \times 2000}{No_{OH}}$$

To terminate with the polyester-diol preparation, it should still be mentioned that other techniques of preparation have been tested and are possible although less preferred, such as the transesterification method in which the starting diol is heated with a lower ester of the diacid and the resulting lower alcohol formed is removed by distillation. This has been tried with diethylene glycol and dimethyl oxalate, the MeOH formed being removed under vacuum. It should also be mentioned that glycol prepolymers can be found commercially, all ready, and can be used in the present method in place of the polyesters made as described above. Also, other polyesters usable in the present invention are described in detail in U.S. Pat. No. 3,778,390. Generally speaking, the range of the polyesters glycols preferably usable in the invention have molecular weights between about 250 and 10,000.

For binding the above polyesterdiols to the catgut core, i.e. to produce a coated sheath on the catgut filament that will properly adhere thereto, isocyanates are preferably used to cap the diols since they can fulfill three main functions: First they can attach to the collagen either by Van der Waals forces or by hydrogen bonds (between the urethane or urea groups derived, after reaction, from the NCO groups and the polypeptide amide functions of the collagen) or by covalency through the reaction of the NCO groups with the free —$NH_2$ groups (lysine) or free OH groups (hydroxyproline) of said collagen. Thus, in the practice of the invention, the polyester-diol will then be capped with diisocyanates (or polyisocyanates if further cross-linking is wanted).

The second function of the isocyanates is to produce some degree of chain extension provided the quantity of diisocyanates used is somewhat less than twice the stoichiometry relative to the diol.

A third function of the isocyanate is to enable what is called "moisture curing" to occur on the freshly coated filament on standing. This operates when the coated film still contains an excess of unreacted NCO groups which can then react with ambiant moisture as follows (R" being any conceptual radical of the isocyanate compound):

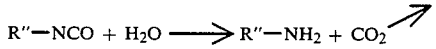

and

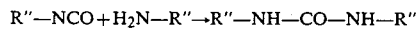

Moisture curing procures a smooth "drying" of the coated finish and contributes also to the excellent properties of the present sheath.

In the present invention, a variety of diisocyanates and polyisocyanates can be used. Aliphatic and cycloaliphatic diisocyanates can be used such as hexane-diisocyanate or cyclohexane-diisocyanate; however, aromatic diisocyanates are preferred because of their higher reactivity: Convenient diisocyanates are p-phenylene diisocyanate, 2,6- and 2,4-toluene diisocyanate (TDI) or p-tolylene diisocyanate. Other suitable di- or poly-isocyanates are disclosed in British Pat. No. 1,430,422, page 3.

The amount of isocyanate compound to be used relative to the diol prepolymer depends on the needs and on the end properties to be given to the sheath. In general, suitable mole ratio of diisocyanate to diol is between 1.1 and 1.5. At lower ratio, the chain extension may become too great before capping becomes effective and the resulting diisocyanate polymer may become too thick for proper coating uses. At the other end, using diisocyanate/diol ratios higher than 1.5 may lead to an excess of free isocyanate groups in the coating material and the end formation of too many urea links after moisture curing which may result in too much rigidity in the sheath. However, the above values are only indicative and may be exceeded, if desired, in both directions.

Generally, the reaction of the prepolymer diol and the diisocyanate is performed by mixing the ingredients at room temperature in a suitable solvent and in the presence or in the absence of a catalyst. A catalyst is advantageous if the reaction must be speeded up but it is not strictly indispensable. As catalysts, tin compounds such as tin octanoate or diaminobicyclooctane (DABCO) of formula

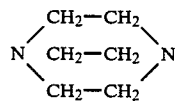

can be used advantageously although other common isocyanate reaction catalyzing materials can also be used. The amount of catalyst is in the range of 0.1 to 5%.

As solvents, the following can be used: toluene, tetrahydrofurane (THF), dioxane, dimethylformamide (DMF), diglyme, ethyl acetate, acetone, cellosolve acetate, methyl-ethyl ketone, pyridine, etc. . . . The solvents must be chosen depending on the needs and on the prepolymer properties, keeping in mind that the higher the molecular weight of the polyester glycol, the less soluble it becomes. Methyl ethyl ketone and cellosolve acetate are, actually, the preferred solvents since they appropriately combine good solvency power and acceptable rates of evaporation from the freshly coated sheath.

In the freshly prepared diisocyanate capped prepolymer solution, the concentration of free isocyanate groups can be analyzed by a method derived from the method described above for determining the free OH of the polyester diol. For this analysis, the isocyanate capped material is weighed exactly (m gram) and a known excess of dibutylamine solution (in toluene) is added. A control blank with solvent only is made similarly, after which both samples are heated for some time and, after cooling, back titration with normal HCl is carried out (indicator: bromocresol green). The percent NCO is then obtained as follows (x mmole of HCl N used):

$$\% \text{ NCO} = \frac{42x}{10m} \quad (MW_{NCO} = 42)$$

In the present invention, with polymer to solvent weight ratios comprised between 0.25 and 1, the percent NCO varied from about 0.35 to 5.2% which means that, in principle, the % free NCO of the undissolved capped prepolymer was about 1.5% to 5.2% by weight depending on the case.

Once the isocyanate capped prepolymer is ready, it can be used for coating catgut filaments by using the coating methods known, in general, by people skilled in the art. Such means include immersion coating, spraying or die coating. A preferred method will be described hereinafter in the Examples. The useful viscosities of the coating solution will be determined by a number of factors such as coating rate, desired coating thickness, type of polymer free isocyanate concentration properties to be given to the coating, etc . . . . In general, proper viscosity values will be obtained by adjusting the polymer to solvent ratio according to the needs. Viscosity values at room temperature of from 50 cP to 200 cP are generally suitable for coating thicknesses ranging from about 1.2 μm to 40-50 μm.

When the filament has been coated with the isocyanate capped polymer, it is allowed to stand for some time to harden in air. During this period, moisture curing occurs, as mentioned hereinabove, which imparts to the sheath its final surface and body properties: softness, slickness, flexibility and modulus. This curing can be carried out in ordinary atmosphere at room temperature or it can be accelerated in a moisture oven between, say 30° and 70° C. If desired, the coating can be repeated for increasing the sheath thickness or for masking the pinholes which may have occured in the first coating. Probabilities that two pinholes superimpose are, indeed, negligible.

When the sheathed catgut is finally ready it is sterilized and packed, either dry or in alcohol containing wrappers for being used in surgery.

Thus, the present invention effectively provides a suture filament with the following useful properties:

(a) It comprises a sleeving that is biodegradable at a rate governed by the coating conditions and the type of polymer used and, depending on the needs, from about 10 hrs to 3-4 weeks.

(b) It has a homogeneous pinhole free layer which protects the core from rapid enzymatic degradation.

(c) It has an appropriate slick surface which enables quick and easy suture work and, simultaneously, prevents knot slippage.

(d) It is simple and cheap to manufacture.

(e) The sleeve has tensile properties under stress comparable with that of the underlying catgut and it does not break when the filament is stretched. Indeed, the coating polymer is slightly more extensible than the core of collagen.

(f) It adheres well to the catgut.

(g) It minimizes tissue reactions after stitching as compared with the effect of normal catgut (chromium treated or not).

REDUCTION TO PRACTICE (Industrial Applications)

The Examples that follow illustrate the invention in which reference is made to the annexed drawing.

FIG. 1 of this drawing represents schematically a device for coating a catgut filament with the capped prepolymer of the invention.

Figure 2:
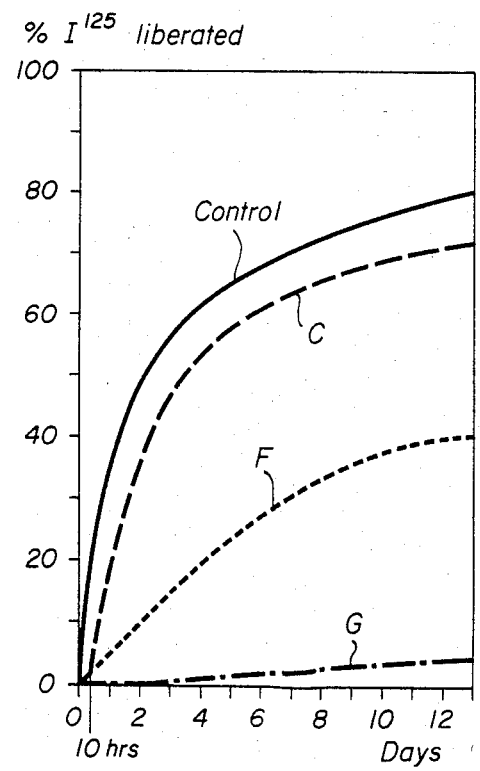

FIG. 2 is a diagram showing the compared resistance to microbiological attack of three sheathed catgut filaments and one unsheathed control.

EXAMPLE 1

There were mixed together under nitrogen 0.0315 mole of perfluoroadipic acid and 0.05 mole of 1,6-hexanediol. The mixture was kept 1.5 hrs at 110° C. and 0.005 g of dry $AlCl_3$ were added (esterification catalyst) and thoroughly mixed after which reduced pressure (0.005 Torr) was applied for evaporating the water formed by condensation. The mixture was finally heated 4 hrs at 200° C. and 1 hr at 235° C. after which it was cooled under dry nitrogen and stored as like. The product was a viscous liquid. Five grams of this prepolymer diol were dissolved with 7.5 ml of THF and 0.5 g of tolylene diisocyanate was added under stirring. After a few minutes rest at room temperature, a polished and untanned catgut filament 0.3 mm thick was coated by dipping into the viscous fluid followed by draining. The solvent was removed with an air jet at 60° C. after which the coated filament was allowed to cure by staying 24 hrs in air at 60° C. For measuring the sheath thickness, the same operations were performed but adding to the polymer solution a small amount of methylene blue. Thus, the coating thickness could thereafter be measured on a microtome cut section of the wire under the microscope by observing the width of the colored circling area. It was found that the coating was about 10 micron thick.

The non-colored coated catgut was tested for degradation on rats as follows: Sheathed and unsheathed control filament lengths (about 4 cm) were stitched under the skin of a series of experimental rats (Sprague Dawley). The controls were chromium treated. After test periods of respectively two, seven and fifteen days some of the test and control rats were sacrificed and the wounds were examined histlogically. It was found that the filaments protected according to the present Example stayed virtually unattacked after two and seven days and that tissue swelling and inflaming was negligible and markedly less than that observed around the chromated catgut filaments after two days. Also, after fifteen days, the sheath of the filaments coated according to the present Example were only partly attacked whereas the control filaments were very strongly degraded.

EXAMPLE 2

Fifty g (0.373 mole) of 2,2-oxydiacetic acid and 44.5 g (0.391 mole) of diethylene glycol were mixed with 0.05 g of $AlCl_3$ and the whole was heated according to the following program:

| Time (hrs) | Temperature (°C.) | Pressure (Torr) |
|---|---|---|
| 1 | 110 | 760 |
| 0.5 | 135 | 760 |
| 1 | 135 | 20 |
| 1 | 135 | 0.05 |
| 4 | 200 | 0.05 |
| 1 | 235 | 0.05 |

The resulting polyester was allowed to cool and was dissolved in dry chloroform, then it was filtered on glass frit to remove the catalyst. The solution was evaporated under vacuum and yielded a colorless waxy material. The $No_{OH}$ value was analyzed as described hereinbefore and found to be 4,650 in rather close agreement with theory. The polyester diol was diluted with methyl ethyl ketone (MEK) or cellosolve acetate to make a 52.5% by weight solution. This was stored as the stock solution.

Aliquots of 3 g (0.0035 mole) of the above polyesterglycol solutions were further diluted with 3 g of MEK (or cellosolve acetate) to produce solutions at 26.3% by weight and to each of the solutions were added a quantity of TDI calculated for having the following mole ratios diisocyanate/diol: (a) 1.1; (b) 1.3; (c) 1.5. To the above solutions were further added 0.25% by weight of polymer solids of DABCO catalyst. The obtained solutions of NCO capped polyester glycol were then used for coating catgut filaments using the device schematically pictured on FIG. 1. This device comprises a cup 1 of stainless steel or any other inert material in the bottom of which a tiny hole 2 has been drilled. The cup is filled with the polymer solution 3 and the diameter of the hole is adapted for enabling a catgut filament 4 to freely pass therethrough but small enough to substantially prevent the polymer solution to drift around the filament through the hole. The catgut 4 is attached to a pulling wire 5 which passes over pulley 6 and can be wound on a roll 7 by means of drive not represented here (motor or crank). For setting the device into operation, the catgut filament is threaded from the bottom through the hole, crimped around the wire 5 and the whole is drawn at constant speed (1 cm/sec in the present Example) until the whole length of the filament has been coated by passing through the cup. The overall dimensions of the device are adjusted for having the coated filament to just overhang from roller 6 without touching it not to disturb the freshly applied coating. Then, the filament is uncrimped and allowed to stand in moist air for hardening. In the present Example this period was about 48 hrs. After this period, the sheath was considered to be fully cured and the surface was smooth and glossy. However, tests made on films cast on glass plates with the same polymer showed the absence of free NCO groups by I.R. spectrometry after already 12 hrs at 40° C. ($\nu_{CN}$ at 2240 $cm^{-1}$). It is interesting to note that the coated catgut filaments thus prepared were substantially transparent whereas non-coated catgut is opaque. This feature which probably results from a proper matching of the refraction indexes of both materials is commercially attractive.

Regarding now the differences obtained with coatings of types (a), (b) and (c) above, it was found that polymerization was faster with the coatings having the highest NCO/OH ratio; not much difference was found in the final properties, however, the (c) sample being somewhat more rigid than the other samples but with not much significance. All samples had very good handling properties for stitching, having no knot slippage and well accomodating catgut swelling when in contact with aqueous fluids. No break of the sheath was experienced during manipulations. The thickness of the coatings, as measured as described above, was in the range of 2–5 μm.

EXAMPLE 3

A series of 6 polyester-diols (respectively, A to F) were prepared from diethylene glycol and oxalic acid for samples A to C and 2,2-oxydiacetic acid for samples D to F but changing the mole ratio diacid to diol in order to obtain different molecular weights for the polyesters. The reaction conditions were that described in Example 2 and the following Table I provides data on the various samples including the values for n (see the introduction) from which the COOH/OH ratios used were calculated and the experimental n calculated, as already described, from the molecular weight determined experimentally.

TABLE I

| Sample | diacid | n (theory) | $NO_{OH}$ | $MW_{OH}$ | n (from No) |
| --- | --- | --- | --- | --- | --- |
| A | oxalic | 1.2 | 390 | 290 | 1.04 |
| B | " | 4 | 146 | 765 | 3.9 |
| C | " | 5 | 135 | 830 | 4.3 |
| D | oxydiacetic | 18 | 26.4 | 4250 | 16.7 |
| E | " | 14 | 34.3 | 3260 | 12.7 |
| F | " | 3 | 173 | 650 | 2.3 |

The polyester diols A to F were all diluted to 26.3% with MEK (or isobutylmethyl ketone) and an amount of TDI was added to have an isocyanate prepolymer solution with an NCO/OH ratio of 1.5 together with 0.25% of DABCO. Then the solutions were used to coat catgut filaments of diameter 0.5 mm with the device described in Example 2 at a speed of 1 cm/sec. After curing the coated filaments were tested for their handling properties by pulling, stitching and knotting. It was found that samples A, B, C and F were all right while samples D and E sleeves had too much elasticity for proper handling this being due to using the higher molecular weight polyesterdiols. Thus, other samples were prepared similar to D and E but replacing 0.05 equivalent of the diethylene glycol by 0.05 equivalent of trimethylolpropane. When capping such modified polyester-glycols with TDI as described above and coating catgut filaments therewith, sleevings were obtained with much reduced elasticity due to the introduction of cross-linking.

EXAMPLE 4

An isocyanate capped polymer solution was prepared corresponding exactly to sample F of the previous Example and, after the addition of 0.5% of bromocresol blue, it was used to coat catgut filament (1.4 m lengths) of various grades (No. 1-0, 2-0 and 3-0 corresponding to thicknesses of 0.40, 0.35 and 0.30 mm, respectively). The coating speed was 1 cm/sec. In some cases the filaments were coated twice (2 passes) after an intermediate curing interval of 30 min. During the interval the isocyanate solutions were kept away from moisture to avoid premature polymerization.

After final curing the coating thicknesses were measured both by weighing (the bare catgut had been previously dried over $P_2O_5$ to constant weight) and under the microscope as described hereinbefore. The results are shown below:

| Filament No | Nb. of passes | Coating thickness (μm) |
| --- | --- | --- |
| 1-0 | 1 | 2 |
| 1-0 | 2 | 6 |
| 2-0 | 1 | 1.5 |
| 3-0 | 1 | 1.2 |
| 3-0 | 2 | 4.5 |

These data show that the second coating operation more than doubles the sheath coating thickness. The advantage of a double coating is to efficiently mask some pinholes which might have possibly formed in the first coating and which would, otherwise, constitute attacking sites for the catgut core.

EXAMPLE 5

Three samples of sheathed catgut C, F and G were prepared by the technique described in Example 2. Samples C and F were identical with the corresponding samples C and F of said Example and sample G was prepared from a similar polymer but using glutaric acid as the diacid, the n value for the intermediate polyester glycol being about 4. The sheath thickness was about 6–8 μm and was composed of a double layer coating (2 passes).

The above three samples were subjected to enzyme degradation testing, together with an uncoated control, as follows:

Prior to coating, a 60 cm long segment of catgut filament (No. 5, 0.5 mm) was coiled in a Petri box and wetted with 3 ml of an alcohol-water buffer at pH 7.5 (0.05M phosphate+0.9% NaCl). After 20 min., the buffer was discarded and there was added into the box a mixture of 1 ml of the buffer and 10 ml of aqueous $Na^{125}I$ (activity 1 mCurie). After agitating for 20 min, there were added 20 μl of chloramine T solution (100 μg), this solution being of 50 mg/l of chloramine T in the above NaCl/phosphate buffer. After further 20 min of agitation, there were successively added 0.1 ml of a $K_2S_2O_5$ solution (at 1.334 g/l in the NaCl/phosphate buffer), then 0.5 ml of a 0.4M KI solution in the same buffer and, finally, 0.5 ml of tert.BuOH. After half an hour, the liquid was removed and the filament was thoroughly rinsed with several portions of 5–6 ml each of the above alcohol-water buffer. Then, the catgut was also rinsed with the normal sterilizing solution for preserving catgut sutures. The length of filament was dried and cut into 4 parts, three of them being coated, including the ends, for making samples C, F and G as said above and the fourth remaining uncoated (control). The samples were then allowed to stand in pH 7.4 buffer for 48 hrs until no further radioactive iodine was liberated. Measurements of radioactivity were performed using a Gamma Radio Spectometer (Packard model 300). In such spectrometer the counting of the total sample (irrespective of its size) is measured. Degradation tests on the samples were performed as follows:

Each filament was placed in a test tube containing 5 ml of a solution at pH 7.4 (0.07M phosphate buffer) containing NaCl (0.08M), $CaCl_2$ (0.01M), $NaN_3$ (0.2 mg/ml), streptomycine sulfate (0.05 mg/ml) and collagenase (0.002 mg/ml). One hundred μl aliquots were removed at time intervals for radio-activity counting of the dissolved $^{125}I$ thus liberated. The measurements were carried out first after hourly periods, thereafter from dayly periods. Each day, the enzyme solutions were replaced by identical fresh solutions. The results are shown on the graph of FIG. 2. This graph plots, against time, the iodine liberated as a percent of the total iodine initially present. The obtained curves are labelled as the sample they illustrate. They show that the oxalic based polymer provided about 10–12 hrs of effective protection after which the core became subjected to enzymatic attack (curve C is about parallel to the control curve). Attack on sample F was much slower, thus providing adequate protection for about two weeks. Sample G (glutaric acid) was fairly inert during the corresponding period.

EXAMPLE 6

Example 2 was repeated but using 75.66 g (0.380 mole) of tetraethylene glycol instead of the diethylene glycol and 0.015 mole of glycerol. The polyester thus obtained was a waxy solid which was treated with 1.5 equivalent of tolylene diisocyanate in DMF to obtain a 18% solids solution of isocyanate prepolymer. This solution was used to coat catgut lengths as described in Example 2. The coated filaments were allowed to dry in air at room temperature for 48 hrs after which they were dipped into water and allowed to stay for 12 hrs for eliminating all traces of DMF. After drying, the filaments had a smooth 10–12 μm coating and had good handling properties.

I claim:

1. A catgut suture filament comprising a catgut core coated with an adherent protective sheath made of a polyester based flexible resin reinforced by urea or urethane links, the sheath being hydrolytically but not enzymatically degradable.

2. The filament of claim 1, wherein the resin is a hydroxylated polyester capped with a polyisocyanate.

3. The filament of claim 1, wherein the resin sheath is based on polyesters containing linear segments derived from at least one glycol selected from the group consisting of aliphatic glycols of from 3 to 12 carbon atoms, cycloaliphatic glycols of from 3 to 12 carbon atoms and polyoxyalkylene glycols containing 2 to 15 polyoxyalkylene units.

4. The filament of claim 3, wherein the resin also comprises branched segments derived from hydroxy-compounds containing more than two —OH groups.

5. The filament of claim 4, wherein the branched segments derived from hydroxy-compounds are selected from the group consisting of triols, tetrols and polyols.

6. The filament of claim 4, wherein the branched segments derived from hydroxy-compounds are selected from the group consisting of glycerol, trimethylolpropane, and hydrogenated monosaccharides.

7. The filament of claim 3, wherein the polyester portion contains segments derived from diacids selected from oxalic acid, malonic acid, succinic acid, glutaric acid, adipic acid, pimelic acid, perfluoroadipic acid, 2,2-oxydiacetic acid, 2-oxoglutaric acid and D-tartaric acid.

8. The filament of claim 1, wherein the adherent protective sheath does not substantially degrade until the wound has had a sufficient time to heal.

9. The filament of claim 1, wherein the adherent protective sheath is bonded to the catgut core by urea or urethane links.

10. The filament of claim 9, wherein the bond is a covalent bond.

* * * * *